(12) United States Patent
Moore, II

(10) Patent No.: US 6,916,852 B2
(45) Date of Patent: Jul. 12, 2005

(54) METHOD FOR REGULATION OF MICROVASCULAR TONE

(75) Inventor: Bob M. Moore, II, Nesbit, MS (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/436,028

(22) Filed: May 12, 2003

(65) Prior Publication Data

US 2004/0229928 A1 Nov. 18, 2004

(51) Int. Cl.$^7$ ...................... A61K 31/164; A61K 31/18
(52) U.S. Cl. ....................................... 514/605; 514/627
(58) Field of Search .............................. 514/605, 627, 514/406, 454

(56) References Cited

U.S. PATENT DOCUMENTS

| | | | |
|---|---|---|---|
| 5,939,429 A | | 8/1999 | Kunos et al. |
| 2004/0010013 A1 | * | 1/2004 | Friary et al. ................ 514/326 |

FOREIGN PATENT DOCUMENTS

| WO | 03/042174 | * | 11/2002 |
|---|---|---|---|

OTHER PUBLICATIONS

Dilger, K., et al., "Effects of Celecoxib and Diclofenac on blood pressure, renal function, and vasoactive prstanoids in young and elderly subjects", J. Clin. Pharmacology, 42:985–994 (2002).

Hillard, CJ, "Endocannabinoids and vascular function", J. Pharmacology and Experimental Therapeutics, 294(1):27–32 ((2000).

Brown, DJ, et al., "The influence of Δ9–tetrahydrocannabinol on cardiovascular and subcutanteous microcirculatory systems in the bat", J. Pharmacology and Experimental Therapeutics, 188(3):624–629 (1974).

Kunos, G. et al., "Endocannabinoids as cardiovascular modulators", Chemistry and Physics of Lipids, 108:159–168 (2000).

Wagner, JA, et al., "Cardiovascular actions of cannabinoids and their generation during shock", J. Mol. Med., 76:824–836 (1998).

Adams, MD, et al., "Vasoconstrictor Actions of ΔB– and Δ9– tetrahydrocannabinol in the rat", J. Pharmacology and Experimental Therapeutics, 196(3):649–656 (1976).

Wagner, JA, et al., "Activation of peripheral CB1 cannabinoid receptors in haemorrhagic shock", Nature, 390:518–521 (1997).

Johnson, DL., et al., "Effect of Cyclooxgenase–2 inhibitors on blood pressure", The Annals of Pharmacology, 37:442–446 (2003).

Kunos, G., et al., "Cardiovascular effects of endocannabinoids—the plot thickens", Prostaglandin & Other Lipid Mediators, 61:71–84(2000).

Lake, KD, et al., "Cannabinoid–Induced hypotension and bradycardia in rats is mediated by CB1–like cannabinoid receptors", J. Pharmacology and Experimental Therapeutics, 281(3):1030–1037 (1997).

Siqueira, SW, et al., "The triple effect induced by Δ9–tetrahydrocannabinol on the rat blood pressure", European Journal of Pharmacology, 58:351–357 (1979).

* cited by examiner

*Primary Examiner*—Phyllis G. Spivack
(74) *Attorney, Agent, or Firm*—Howard Eisenberg, Esq.

(57) ABSTRACT

Methods and kits for regulating arterial microvascular tone in which a COX-2 inhibitor and a cannabinoid receptor agonist are co-administered to a subject.

26 Claims, 3 Drawing Sheets

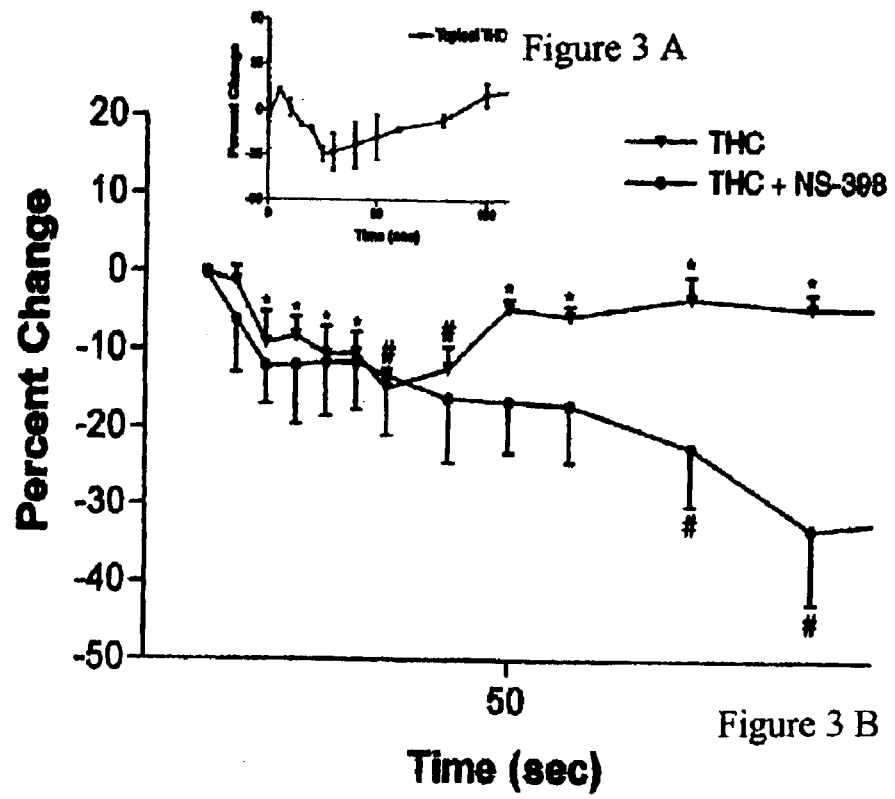
Figure 3 A
Figure 3 B
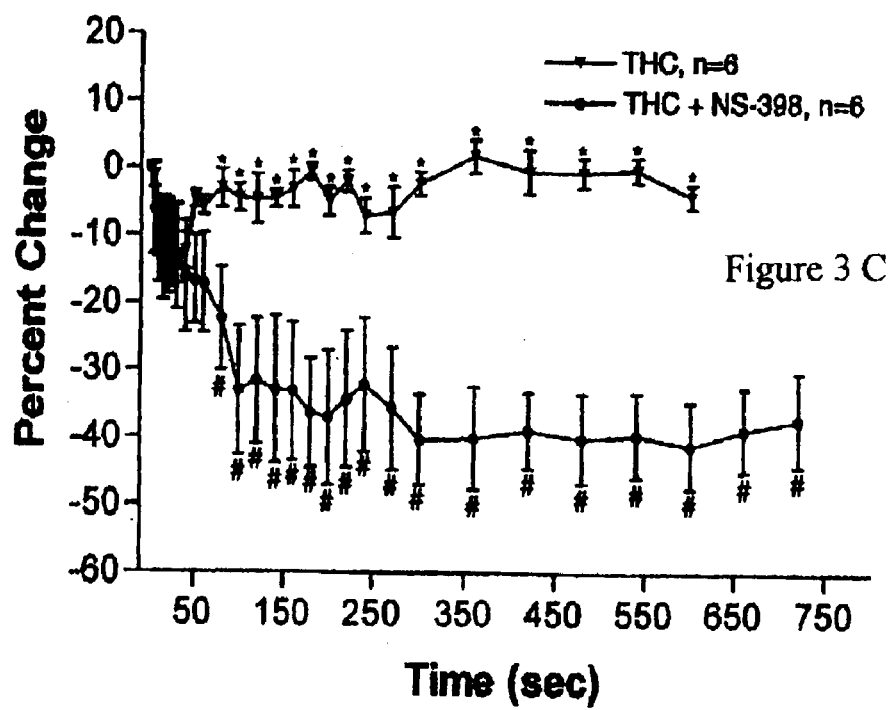
Figure 3 C

METHOD FOR REGULATION OF MICROVASCULAR TONE

FIELD OF THE INVENTION

The invention pertains to the field of administration of pharmacologic chemical compounds to regulate the tone of small blood vessels.

BACKGROUND OF THE INVENTION

The circulatory system in humans and other vertebrate animals includes a heart, which pumps blood throughout the body, and a vascular system, which is a series of tubes supplying blood to all regions of the body. The blood leaves the heart through arteries, which transport the blood under high pressure to the tissues of the body. Blood returns to the heart from the tissues through veins. The arteries repeatedly subdivide into progressively thinner tubes and eventually give rise to arterioles. The arterioles feed into capillaries, which are thin walled structures through which oxygen exchange occurs within tissues. Blood from the capillaries then enters small venous structures called venules, which merge repeatedly to form veins, which carry the blood back to the heart. Collectively, the arterioles, capillaries, and venules are referred to as the "microvasculature".

The arterioles, unlike the other portions of the microvasculature, have smooth muscle fibers in their walls. These fibers regulate blood flow into and through the microvasculature by contracting and dilating as needed. In this way, the arterioles control the distribution of blood in the body and maintain systemic blood volume and arterial blood pressure within physiologic limits.

Shock is a progressive, widespread reduction in tissue perfusion that results from a decrease in effective circulating blood volume causing a decrease in oxygen delivery and exchange within capillaries. If untreated, shock is often fatal.

Shock may be due to several causes, which has led to the classification of shock into several categories. Thus, shock due to loss of blood volume due, for example, to hemorrhage or to microvascular blood pooling, is termed hypovolemic shock. Shock due to failure of the heart to adequately pump blood throughout the body is termed cardiogenic shock. Shock has also been classified as being vasogenic, that is due to a maldistribution of blood to the tissues, such as due to acute vasodilation without a concomitant increase in intravascular volume, resulting in inadequate tissue perfusion. Vasogenic shock is seen with shock due to sepsis, anaphylaxis, and neurogenic injury. Regardless of the cause of shock, however, if untreated shock can lead to severe complications including myocardial depression, acute respiratory distress, renal failure, disseminated intravascular coagulation, and death.

Shock is treated by diagnosing and correcting, if possible, the underlying cause of the shock, such as by controlling bleeding or re-starting the heart, treating the effects of shock, such as administering oxygen and correcting acid-base imbalance, and by supporting vital functions, such as by administering fluids to maintain blood pressure and heart function. Medications that are useful in combating shock include inotropic drugs to increase the strength of cardiac contraction, corticosteroids which stabilize membranes, vasopressors which cause constriction of blood vessels and thus help to maintain arterial blood pressure, and narcotics to relieve pain and anxiety associated with shock.

However even with such treatment, severe shock, due to any or a combination of causes, may progress and result in permanent complications or death. Thus, there is an ongoing need to develop new and additional methods for treating and for preventing shock.

Cannabinoids are a class of chemical compounds that are naturally produced in plants and in animals. Plant produced cannabinoids include $\Delta^9$-tetrahydrocannabinol (THC) and $\Delta^8$-tetrahydrocannabinol, the first of which is the psychotropic principle in marijuana. Cannabinoids that are endogenously produced in animals are referred to as endocannabinoids, and include arachidonyl ethanolamide (anandamide) and 2-arachidonyl glycerol (2-AG). Additionally, there are a large number of synthetic cannabinoid analogs, including synhexyl, nabilone, and non-classical cannabinoids, such as CP55940, aminoalkylindole (WIN 55212), and diarylpyrazoles.

Kunos, et al., U.S. Pat. No. 5,939,429, incorporated herein by reference, discloses that cannabinoids may be useful in treating hemodynamic abnormalities such as hypotension or hypertension. As disclosed in Kunos, administration of a cannabinoid receptor agonist, such as anandamide, causes hypotension. Conversely, administration of a cannabinoid receptor antagonist, such as SR141716A, prevents anandamide-induced hypotension. Thus, Kunos concluded that the use of a drug that selectively blocks cannabinoid receptors will be of therapeutic value by preventing or attenuating endotoxin-induced hypotension. Additionally, because agonists of cannabinoid receptors lower blood pressure, Kunos concluded that such agents could be used to treat conditions associated with excessive vasoconstriction, such as hypertension, peripheral vascular disease, or angina pectoris.

The hypotensive effect of cannabinoids has been reported widely in the scientific literature. Each of the following scientific references is incorporated herein by reference and discloses that cannabinoids cause hypotension when administered to animals. (1) Kunos, G., et al., *Prostaglandins & other Lipid Mediators*, 61:71–84 (2000); (2) Lake, K D, et al., *Journal of Pharmacology and Experimental Therapeutics*, 281(3):1030–1037 (1997); (3) Hilliard, C J, *Journal of Pharmacology and Experimental Therapeutics*, 294(1):27–32 (2000); (4) Brown, D J, et al., *Journal of Pharmacology and Experimental Therapeutics*, 188(3):624–629 (1974); (5) Adams, M D, *Journal of Pharmacology and Experimental Therapeutics*, 196(3):649–656 (1976); (6) Kunos, G, et al., *Chemistry and Physics of Lipids*, 108:159–168 (2000); (7) Wagner, J A, et al., *Journal of Molecular Medicine*, 76:824–836 (1998); (8) Siqueira, S W, et al., *European Journal of Pharmacology*, 58:351–357 (1979); and (9) Wagner, J A, et al., *Nature*, 390:518–521 (1997). Adams, reference (5) above, discloses that, although intravenously administered $\Delta^9$-tetrahydrocannabinol or $\Delta^8$-tetrahydrocannabinol caused decreases in blood pressure, intra-arterially administered $\Delta^9$-tetrahydrocannabinol or $\Delta^8$-tetrahydrocannabinol produced an increase in blood pressure indicative of vasoconstriction. When administered intravenously, Adams reports that THC produced a transient increase in blood pressure that lasted only about one minute and that was followed by a more prolonged hypotensive response. Wagner, reference (8) above, discloses that administration of the cannabinoid THC or HU-210 doubled survival time from about 30 minutes to 60 minutes in rats that were subsequently bled. Wagner states that the mechanism for this improvement in survival is unclear and speculates that it may be due to a favorable redistribution of cardiac output or improved microcirculation by localized vasodilation.

Kunos, U.S. Pat. No. 5,939,429, further suggests that activation of cannabinoid receptors may be beneficial for survival in hemorrhagic shock, probably because the hypotension caused by the cannabinoid agonist counters the excessive compensatory hypertension that occurs following hemorrhage. It is because of this vasodilatory effect that cannabinoid receptor agonists are suggested to be useful in the treatment of hemorrhagic shock and other conditions associated with excessive vasoconstriction, such as hypertension, peripheral vascular disease, and certain forms of angina pectoris.

Information on the blood pressure effects of COX-2 inhibitors is inconclusive. Johnson, D L, *The Annals of Pharmacotherapy*, 37:442–446 (March 2003) reported on several studies of the effects of COX-2 inhibitors on blood pressure and on reports of elevated blood pressure as an adverse effect of COX-2 inhibitors. Johnson discloses that were inconclusive. Short-term trials suggested that COX-2 inhibitors have no effect on blood pressure on normotensive patients, although these studies may have been flawed because the study subjects were restricted to a low-sodium diet. In another study in which patients were administered either rofecoxib or celecoxib for six weeks, rofecoxib was found to elevate blood pressure and the results on celecoxib were inconclusive. Johnson also reported that some limited data suggests that blood pressure may increase following initiation of therapy with COX-2 inhibitors. Johnson concluded by stated that despite the information provided, it is currently unknown whether an association exists between COX-2 inhibitor therapy and blood pressure elevations. Johnson did not disclose or suggest any effect of COX-2 inhibitors on arterial microvasculature.

Dilger K., et al., *Journal of Clinical Pharmacology*, 42:985–994 (2002) evaluated the effects of celecoxib, a specific COX-2 inhibitor, and diclofenac, a non-specific COX inhibitor, on blood pressure, renal function, and vasoactive prostanoids in both young and elderly patients. Dilger concluded that their study provided evidence that therapeutic doses of either celecoxib or diclofenac given for 15 days are apparently not associated with significant changes in blood pressure or renal function in healthy young or elderly subjects. Dilger did not disclose or suggest any effect of COX inhibitors on arterial microvasculature.

To date, other than the Adams reference (5) described above which discloses intra-arterial administration of THC, there have been no published reports on the use of either a cannabinoid receptor agonist or a COX-2 inhibitor to cause constriction of arterial microvasculature.

DESCRIPTION OF THE FIGURES

FIGS. 3A to C is a series of graphs showing, respectively, the vasoactive response of an arteriole following the administration of a cannabinoid, the vasoactive response of an arteriole during the initial 100 seconds following the administration of a COX-2 inhibitor and a cannabinoid, and the vasoactive response of this arteriole for a period of 12.5 minutes following the administration of the COX-2 inhibitor and the cannabinoid.

FIGS. 5A and B is a pair of graphs showing, respectively, the vasoactive response of an arteriole to topically and systemically administered cannabinoid, with and without a COX-2 inhibitor.

DESCRIPTION OF THE INVENTION

Figure 1:
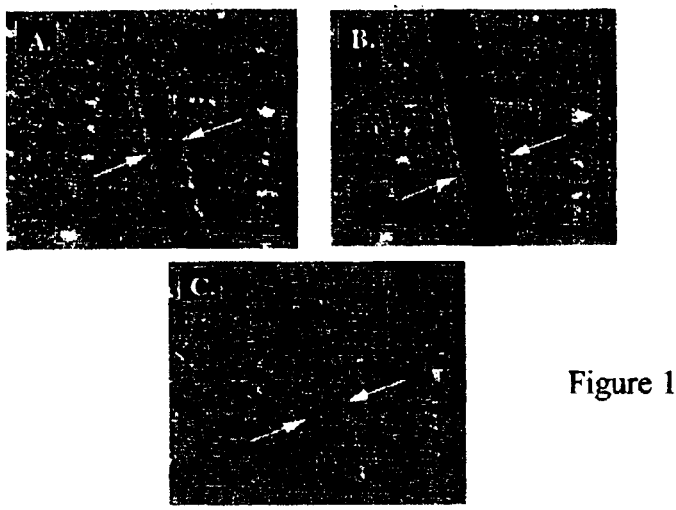
FIGS. 1A to C is a series of intravital microscopic images showing, respectively, an arteriole prior to treatment, the arteriole following administration of an agent that causes arteriolar dilation, and following co-administration of a cannabinoid and a COX-2 inhibitor.

It has been unexpectedly discovered that the microvascular tone, particularly of striated muscle, may be regulated by using a combination of a COX-2 inhibitor and a cannabinoid receptor agonist (CRA). This combination provides a synergistic effect when administered to a vertebrate animal and produces a pronounced, prolonged constriction of arterial microvasculature, especially in the microvasculature of striated muscle. While not wishing to be bound by theory, it is conceived that the combination of COX-2 inhibitor and CRA has a preferential effect in causing constriction of arterial vasculature of striated muscle while having a lesser effect in the splanchnic vasculature. This results in a shunt of blood flow away from skeletal and other striated muscle, which makes a greater volume of blood available for other organs, such as vital organs like the brain and abdominal organs.

In one embodiment, the invention is a method for causing constriction of arterial microvasculature in a vertebrate subject. According to this embodiment, a cannabinoid receptor agonist, hereafter referred to as a cannabinoid or a CRA, is co-administered with a COX-2 inhibitor to a subject in a combined dose effective to cause constriction of arterial microvasculature within the subject.

In another embodiment, the invention is a method for countering the tendency of an administered CRA to cause dilation of arterial microvasculature in a vertebrate subject. According to this embodiment, a COX-2 inhibitor is co-administered with the CRA to a subject in a dose effective to reduce or to block the dilation that would occur if the CRA were administered without the COX-2 inhibitor. Thus, according to this embodiment of the invention, co-administration of a COX-2 inhibitor and a CRA causes a lesser drop in blood pressure compared to that which would otherwise occur following administration of a CRA alone.

In another embodiment, the invention is a method for increasing blood pressure in a vertebrate subject. According to this embodiment, a CRA is co-administered with a COX-2 inhibitor to a subject in a combined dose effective to cause an increase in the blood pressure of the subject. In a preferred embodiment, at the time of the co-administration, the subject is suffering from an acute decrease in blood pressure.

In another embodiment, the invention is a method for treating a bodily disorder associated with hypotension. According to this embodiment, a CRA is co-administered with a COX-2 inhibitor to a vertebrate subject suffering from such a disorder or to a subject at risk of suffering from such a disorder in a combined dose effective to cause an increase in the blood pressure of the subject or to prevent a decrease in the blood pressure of the subject.

In another embodiment, the invention is a kit for regulating microvascular tone. According to this embodiment, the kit includes a package containing a COX-2 inhibitor and a CRA, either in separate containers or combined within a single container. Preferably, the kit further contains instructions for co-administering the COX-2 inhibitor and the CRA to a patient in need thereof in order to achieve any or all of the aims of the above-described methods.

The invention, in any or all of its embodiments, is useful in both a therapeutic and experimental situations. For example, the invention may be used to control acute hypotension, such as that associated with disorders like shock. The invention may also be used to control acute hypotension associated with idiosyncratic reactions to the administration of general, spinal, or epidural anesthetic agents.

The method of the invention is useful in any animal that has a circulatory system containing a splanchnic and striated arterial microvasculature. Thus, the invention is useful in vertebrates, including non-mammal vertebrates such as fish, amphibians, reptiles, and birds. The invention is useful in mammals, such as domestic or non-domestic felines, canines, ungulate ruminants and non-ruminants, non-ungulate ruminants, rodents, lagomorphs, pinnipeds, and human and non-human primates. Further, because interspecies responses to COX-2 inhibitors and to cannabinoid receptor agonists is conserved, data obtained in animal studies relating to responses to either or both of these chemical compounds is applicable to humans.

As used in this specification, the term "COX-2 inhibitor" refers to those chemical agents that inhibit the cyclooxygenase (COX) activity of the inducible isoform of prostaglandin H synthase. For purposes of this specification, a COX-2 inhibitor may have effects other than inhibition of cyclooxygenase-2. For example, a COX-2 inhibitor that is suitable for the present invention may also inhibit the COX-1 isoenzyme or have additional pharmacologic effects unrelated to cyclooxygenase-1 or cyclooxygenase-2. Thus for example, indomethacin, a chemical compound that binds to both COX-1 and COX-2 enzymes, is suitable, although not preferred, as the COX-2 inhibitor of the invention. Similarly, other chemical compounds that are non-specific COX-1 and COX-2 inhibitors, such as piroxicam, brand name FELDENE™ (Pfizer, New York, N.Y., USA) and tenoxicam, are conceived to be suitable for the present invention.

Examples of COX-2 inhibitors that are suitable for present invention include rofecoxib, brand name VIOXX™ (Merck & Co., Inc. Whitehouse Station, N.J., USA); celecoxib, brand name CELEBREX™ (Pfizer); valdecoxib, brand name BEXTRA™ (Pharmacia Corp., Peapack, N.J., USA); paracoxib, brand name DYNASTAT™ (Pharmacia Corp.); etoricoxib, brand name ARCOXIA™ (Merck & Co., Inc.); NS-398 ((N-(2-cyclohexyloxy-4-nitrophenyl) methane sulphonamide); as well as other COX-2 inhibitors, either those that are presently known or those that will be discovered in the future.

As used in this specification, the terms "cannabinoid" and "cannabinoid receptor agonist", which is often abbreviated "CRA", are synonymous. A CRA is a chemical compound that is an agonist ligand of a cannabinoid receptor, either or both of cannabinoid CB-1 or CB-2 receptors. Preferably, the CRA binds to and is an agonist of the CB-1 receptor. CRAs that are suitable for the invention include plant cannabinoids such as $\Delta^9$-tetrahydrocannabinol (THC) and $\Delta^8$-tetrahydrocannabinol, endogenous cannabinoids known as endocannabinoids such as anandamide (ANA) and 2-arachidonyl glycerol (2-AG), synthetic cannabinoids including both classical and non-classical cannabinoids, and cannabinoids that are presently known or that are discovered in the future. An example of a preferred CRA is methanandamide.

As used herein, the term "co-administer" as it pertains to a COX-2 inhibitor and a CRA means to administer the COX-2 inhibitor and the CRA to a subject at the same time or close enough in time so that the combination of the COX-2 inhibitor and the CRA will provide its synergistic effect. Thus, the COX-2 inhibitor and the CRA may be administered simultaneously, which is preferred. Such simultaneous administration may be by combining the COX-2 inhibitor and the CRA in the same administrating device such as a syringe or by simultaneous administration from different administrating devices. Alternatively, co-administration may by administration of the COX-2 inhibitor followed by administration of the CRA, or by administration of the CRA followed by administration of the COX-2 inhibitor.

As used herein in reference to the effects of administration of a CRA, a COX-2 inhibitor, or the combination of a CRA and a COX-2 inhibitor, an acute vasoactive effect is one which occurs as a direct result of the administration on the arterial microvasculature. This is in contrast to a chronic or long-term effects on blood pressure of the administration of either or both of the CRA and the COX-2 inhibitor, such as due to a change in glomerular filtration or sodium retention which would cause a change in blood pressure typically occurring over an extended course of treatment.

In accordance with the method of the invention, a CRA and a COX-2 inhibitor are co-administered to a patient in need thereof at a combined dosage effective to cause a constriction of striated muscle arterial microvasculature. The co-administration may be before a subject suffers a decrease in blood pressure, such as prior to anesthesia or following a wound but before sufficient blood has been lost to cause a significant drop in blood pressure, or may be following a decrease in blood pressure, such as in a patient suffering from shock, such as hemorrhagic or other cause of shock.

The amount of each of these two pharmacological agents, the CRA and the COX-2 inhibitor, will vary depending upon several factors, including the size of the patient, whether the administration is provided following the onset of loss of blood pressure or in order to prevent a loss of blood pressure in an at-risk individual, and the particular CRA and COX-2 inhibitor that are utilized.

Generally, the preferred amount of CRA that is administered is that which, without a COX-2 inhibitor, causes a response in the microvasculature of striated muscle. Thus, the preferred amount of $\Delta^8$-THC to be administered is about 8 mg/kg or higher, more preferably, 10 mg/kg or higher, and most preferably 12 mg/kg. However, lower amounts of $\Delta^8$-THC may be used in accordance with the invention, if desired, for example if such lower doses provide a constriction of arterial microvasculature, alone or when co-administered with a COX-2 inhibitor.

Generally, the preferred amount of COX-2 inhibitor that is administered is the dosage that is stated in the literature. For example, a preferred dosage of celecoxib disclosed in the Physicians Desk Reference, Medical Economics Company, Inc., Montvale N.J., USA (2001), to be about 100 to 200 mg, which is about 1 to 2 mg/kg. However, lower amounts of celecoxib may be used in accordance with the invention, if desired, for example if such lower doses provide a synergistic effect when co-administered with a CRA.

In accordance with the invention, there is no maximum of either the CRA or the COX-2 inhibitor that is administered. Such maximum dosage of administration is limited, however, by the potential of the occurrence of unwanted pharmacologic effects at high doses.

Constriction of arterial microvascular may be determined by any means that is known or is to be discovered. Such means may be direct or indirect. For example, constriction of arterial microvascular may be determined by studies on the hemodynamic effect in whole animals, perfused vascular beds, or on isolated segments of arteries. Such studies are not preferred because they do not definitively establish that the hemodynamic effect is caused by arteriolar vasoconstriction or do not definitively establish that the response obtained would be that obtained in an intact, whole animal.

Thus, it is preferred that constriction of arterial microvasculature be determined by a technique that provides direct real-time visualization and assessment of microvasculature in vivo. One such technique is intravital microscopy. See, Koller, A. and Johnson, P C, *Methods for in vivo mapping and classifying microvascular networks in skeletal muscle*, eds. Popel, A S and Johnson P C, Karger, New York (1986), incorporated herein by reference.

The invention is further illustrated in the following non-limiting examples.

EXAMPLE 1

Cremaster Muscle Protocol

Male C57-BL mice age 7–8 weeks and weighing approximately 20 grams are anesthetized with an intramuscular injection of 100 to 150 microliters of a mixture of ketamine and xylazine (87 mg ketamine and 13 mg xylazine per ml) based on the weight of the individual animal. The body temperature was maintained at about 37° C. by convective heating. The animal is supinated, a midline incision is made in the ventrocervical region, and the underlying tissues are bisected laterally to expose the trachea. A tracheotomy is performed and the animal is intubated directly with PE50 tubing to facilitate ventilation. The wound is then closed.

The left rear limb is incised to expose the femoral neurovascular bundle and the femoral vein is isolated and catheterized with PE10 tubing attached to a syringe containing normal saline. The animal is then placed on a specially designed surgery board and the right testicle within the scrotum is oriented over a translumination observation window contained in the surgery board. The scrotum is irrigated with warmed (about 37° C.) physiological saline (4.3 mM $NaHCO_3$, 126.4 mM NaCl, 0.9 mM KCl, 0.4 mM $CaCl_2$, 0.2 mM $MgSO_4$). The scrotum is incised medially and the underlying fascia is bluntly dissected to expose the testicle. The apical portion of the cremaster muscle is pinned distally on the surgery board and the cremaster muscle is incised along its long axis to expose the testicle. The testicle is then gently forced back into the inguinal canal, allowing the cremaster muscle to be pinned evenly around the translumination window.

EXAMPLE 2

Mesentery Protocol

Animals as described in Example 1 are prepared for surgery as described in Example 1. The animal is supinated on the surgery board so that the ventral portion of the animal faces the observation window. Upon irrigation with warmed physiological saline, a midline incision is made through the linea alba. A loop of small intestine from the lower duodenal segment is extracted and pinned around the observation window, with the pins passing through the proximal mesentery and not through the intestine proper.

EXAMPLE 3

Intravital Microscopy

All experiments are carried out using an industrial grade microscope (Nikon MM-11) with two light sources, bright field (OptiQuip 75 W xenon) and fluorescent (Nikon 150 W mercury). The primary camera assembly has a chilled charged coupled device (CCD) and controller (Hamamastu C5985). The secondary camera assembly has a CCD camera (MTI CCD72) in conjunction with an intensifier (MTI GENIISYS). Experiments are viewed on a video monitor and recorded on a digital video recorder for off-line processing.

The prepared animal, as described above in Examples 1 and 2, is placed on the stage of the microscope on the surgery board with the translumination window. Exposed tissues are irrigated with warmed physiological saline through which a $N_2/CO_2$ (95%/5%) mixture is bubbled. The tissue is allowed to equilibrate until normal blood flow is observed or perfusate flow stabilizes, during which time the tissue is scanned at 1-X for A1-A4 arterioles. The arterioles are then tested for physiological tone by the topical administration of 0.1 mM adenosine (positive control). Vessels that do not demonstrate at least a 20% increase in diameter are not considered for the experiment.

After the arteriole returns to resting diameter (about 10 minutes) the tissue is treated topically with test chemical drugs or the drugs are administered systemically and the responses of the arterioles are viewed at 20× magnification. Topical treatment is by directly applying a vehicle solution (1:1:18 stepantex:ethanol:saline) or a drug plus vehicle solution. Systemic treatments in the whole animal are administered through the femoral vein catheter. The arteriole is video recorded during the entire procedure for off-line analysis. The blood pressure is monitored throughout the procedure utilizing a 1.4 F (0.56 mm) Millar catheter pressure transducer inserted into the left ventricle via the aorta. Systolic and diastolic blood pressure, and heart rate are recorded. Drug dosing regimens for the animals are based on literature values or values experimentally determined via drug titration curves on a mg/kg basis.

EXAMPLE 4

Data Analysis

The video images of Example 3 are analyzed off-line by first converting the digital AVI files into digital image files followed by analysis using MetaMorph software (Universal Imaging Co.) on a Dell Optiplex GX-1. Calibration of the software is done using a micrometer slide and measurements are defined in micrometers/pixel. An average of 5–6 measurements per time point per vessel are made at initial intervals of 5 seconds for the first 50 seconds followed by increasing interval length. This methodology is held constant for both the 180-second control injections and the subsequent cannabinoid injections.

Data analysis is carried out using GraphPad, Prism software. The significance of the change in vessel diameter between time points, experiments, and conditions is determined via an analysis of variance. A statistically significant variation in diameter or percent change is defined as $P<0.05$ with n=5 or more. Time course curves are fit using non-linear regression from which the rate of vessel constriction or dilation is calculated.

EXAMPLE 5

Drug Administration Protocol

A vehicle solution of stepantex:ethanol:isotonic saline (1:1:18) is utilized to prepare the drug solutions. Lipophilic drugs are first dissolved in stepantex:ethanol (1:1), then combined with the isotonic saline. Hydrophilic drugs are dissolved directly in the stepantex:ethanol:isotonic saline solution.

Prior to administering test drugs (CRA, COX-2 inhibitor, or combination), a probe constituted of a CRA with an enzyme inhibitor or a cannabinoid receptor antagonist is systemically administered followed 3 minutes later by the test drug, either systemically administered or topically applied. This permits the identification of tissue specific responses and a correlation of the local effects to those of the systemic effects. The dosage of THC and NS-398 that is systemically administered in the following examples is 12 mg/kg THC and 2 mg/kg NS-398.

EXAMPLE 6

Intravital Microscopy of Arteriole

FIG. 1A to C shows frames taken from an intravital microscopy experiment on a cremaster arteriole as performed as described in the Examples above. The arteriole is imaged in a resting state, before administration of chemical agent, as shown in FIG. 1A. Dilation of the arteriole is observed in FIG. 1B following topical administration of adenosine, an agent that causes arteriolar dilation. Constriction of the arteriole is observed in FIG. 1C following administration of the combination of the cannabinoid THC and the COX-2 inhibitor NS-398.

EXAMPLE 7

Arteriolar Response to COX-2 Inhibitor

Figure 2:
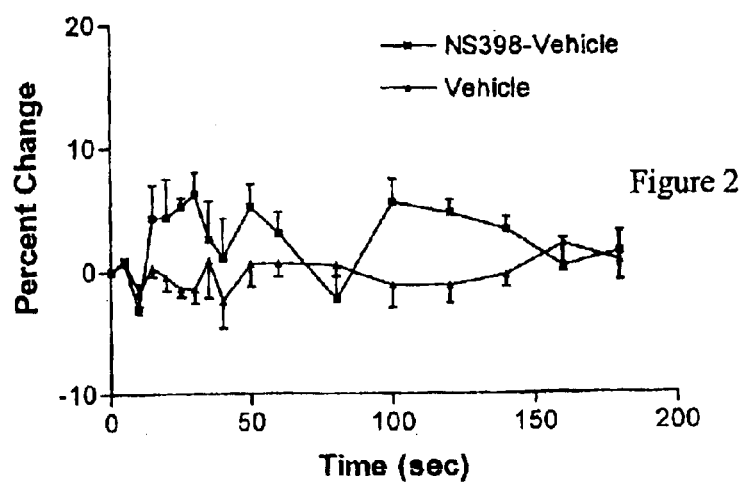
FIG. 2 is a graph showing the vasoactive response of an arteriole to a COX-2 inhibitor compared to control.

The response of cremaster arterioles is illustrated graphically in FIG. 2, which is a plot of percent change in arteriolar diameter over time in seconds. Cremaster arterioles exposed to systemically administered vehicle show essentially no change in diameter within a three-minute period following administration. When NS-398 is administered to mice with the vehicle, an initial mild dilation of the arteriole, about an 8% increase in diameter, is observed, with a return to baseline within about 3 minutes.

EXAMPLE 8

Arteriolar Response to CRA With and Without a COX-2 Inhibitor

The effects of a CRA on cremaster arterioles, alone and in combination with a COX-2 inhibitor is studied and shown graphically in FIG. 3. FIG. 3 is three graphs showing percent change in arteriolar diameter over time in seconds. FIG. 3C compares the change in cremaster arteriolar diameter following systemic administration of $\Delta^8$-THC, referred to in these Examples as "THC" and of THC in combination with NS-398. As shown in FIG. 3C, the combination of the CRA (THC) and COX-2 inhibitor (NS-398) produces a pronounced and prolonged constriction of cremaster arterioles of about a 45% decrease in arteriolar diameter lasting for the entire duration of the experiment of 750 seconds (12.5 minutes).

The initial 100 seconds of the graph of FIG. 3C are shown in an expansion graph, FIG. 3B. This graph clearly shows that both the CRA and the CRA in combination with the COX-2 inhibitor cause an initial mild constriction of about 15% in the arterioles. At about 30 seconds post-administration, however, the diameter of the cremaster arterioles in the mice receiving only the CRA return to baseline diameter. In contrast, the diameter of the cremaster arterioles in the mice receiving both the CRA and the COX-2 inhibitor continues to decrease.

In order to rule out systemic effects on the microvascular diameter, THC is applied topically to cremaster arterioles. As shown in FIG. 3A, the response to topical THC on cremaster arterioles mirrors that of the response to systemic administration of THC, as shown in FIG. 3B.

EXAMPLE 9

Response of Mesentery Arteriole to CRA

Figure 4:
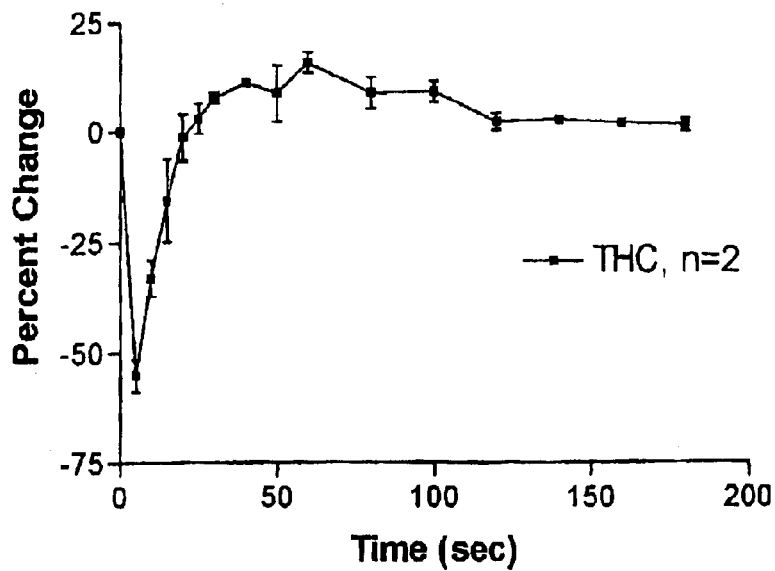
FIG. 4 is a graph showing the response of mesenteric arterioles to a cannabinoid.

Following the protocol described above in Example 2, THC is administered topically to mesenteric arterioles. As shown in FIG. 4, topical administration of a CRA produces a different response in mesenteric arterioles than in cremaster arterioles. CRA administration to mesenteric arterioles produces a biphasic response of an initial brief constriction lasting less than 5 seconds followed by a dilatation and then a return to baseline by about 100 seconds post administration. The response of mesenteric arterioles to CRA administration is consistent with previous reports in the scientific literature.

EXAMPLE 10

Arteriolar Response to Anandamine With and Without NS-398

Figures 5, 6:
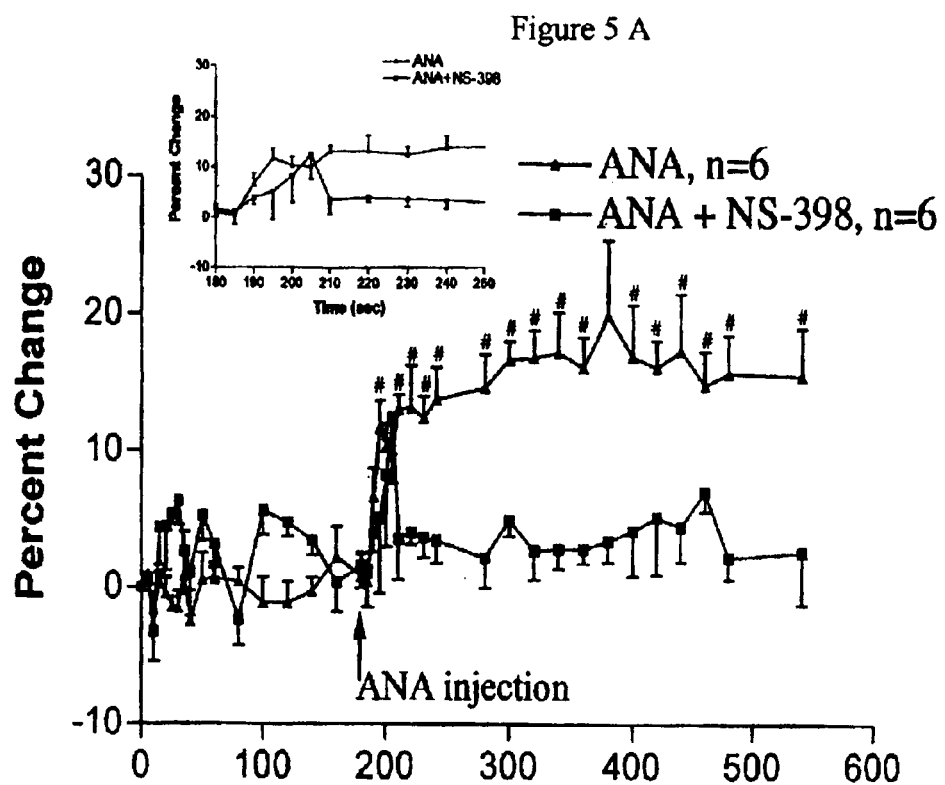
FIG. 6 is a graph showing the change in blood pressure following the onset of stepwise bleeding in untreated rats and in rats treated with the combination of a cannabinoid and a COX-2 inhibitor. Arrow 1 indicates the point where 40 mm Hg is reached and arrow 2 indicates the point of injection of drug or vehicle.

FIG. 5A is a graph showing the percentage change in cremaster arteriolar diameter over time to topically administered anandamide (ANA) with and without NS-398. FIG. 5B is a graph showing the percentage change in cremaster arteriolar diameter over time to systemically administered ANA with and without NS-398. As shown in FIG. 5, ANA, whether administered topically or systemically, causes a dilatation of cremaster arterioles by about 200 seconds post-administration. FIG. 5 further shows that co-administration of NS-398 with ANA blocks the arteriolar dilatation caused by ANA.

EXAMPLE 11

Hemorrhagic Shock

Twelve four-month old Sprague-Dawley rats weighing 300 to 350 grams are subjected to standardized, stepwise bleeding in accordance with the rat hemorrhagic shock model developed by Collins, J A, Arch. Surg., 99:484–487 (1969) as modified by Wagner, J A, Nature, 390:518–521 (1997). The rats are immobilized with isofluorane (0.7 g/kg intraperitoneally) followed by anesthesia with urethane (0.3 g/kg intravenously) or with 300 to 350 microliters intramuscularly of the combination of ketamine (87 mg/ml) and xylazine (13 mg/ml). Body temperature is maintained at about 37° C. by convective heating.

The rats are restrained in the supine position by typing the hind legs to a mounting board. The groin area is shaved on the left limb and is incised to reveal the femoral neurovascular bundle. The left femoral vein and artery are cannulated with P50 tubing which is tied firmly in place using a 4-0 silk thread. A midline incision is made in the ventro-cervical region and the underlying tissues are bisected laterally to expose the carotid artery. A 1.4 F (0.56 mm) Millar catheter pressure transducer, firmly tied into place using 4-0 silk thread, is inserted into the artery to monitor blood pressure and heart rate. The left femoral vein is used for drug injections and the left femoral artery is used for bleeding and sampling.

The animals then undergo a step-wise bleeding until the mean blood pressure stabilizes at 40 mm Hg (removal of about 2 to 2.5 ml of blood). After 5 to 10 minutes at this pressure, the animal is injected with 200 microliters of vehicle (control animals) or a binary drug solution in the same vehicle to provide a dose of 12 mg/kg CRA (THC) and 2 mg/kg COX-2 inhibitor (NS-398). Blood pressure and heart rate are monitored throughout the study. The end point of the experiment is identified when either heart arrhythmia and apnea begin or when the blood pressure drops below 20 mm Hg. At this point, the animal is in severe distress and is euthanized via intra-cardiac injection of saturated KCl.

The results of this study are illustrated graphically in FIG. 6 which compares the arterial blood pressure of rats subjected to hemorrhagic shock as described above and either treated in accordance with the invention by co-administration of a COX-2 inhibitor and a CRA or not so treated. Arrow 1 in FIG. 6 indicates the point in time where blood pressure drops to 40 mm Hg. Arrow 2 indicates the point in time where either a vehicle or the drug combination of the invention is injected.

As shown in FIG. 6, blood pressure in rats not treated in accordance with the invention but rather receiving vehicle continues to drop to below 20 mm Hg by about 40–50 minutes following the onset of stepwise bleeding. In contrast, blood pressure in rats treated in accordance with the invention does not drop below the blood pressure (40 mm Hg) at the time of injection of the combination of COX-2 inhibitor and CRA. In fact, blood pressure rises following this injection and remains elevated above this blood pressure for at least 6 hours, at which time the study is terminated.

Further modifications, uses, and applications of the invention described herein will be apparent to those skilled in the art. It is intended that such modifications be encompassed in the claims that follow.

What is claimed is:

1. A method for causing constriction of arterial microvasculature comprising co-administering to a vertebrate subject an effective amount of a cannabinoid receptor agonist and a COX-2 inhibitor.

2. The method of claim 1 wherein the subject is a mammal.

3. The method of claim 2 wherein the mammal is a human.

4. The method of claim 1 wherein the COX-2 inhibitor is also a COX-1 inhibitor.

5. The method of claim 1 wherein the COX-2 inhibitor is selected from the group consisting of rofecoxib, celecoxib, valdecoxib, paracoxib, etoricoxib, and NS-398.

6. The method of claim 1 wherein the cannabinoid receptor agonist is $\Delta^9$-tetrahydrocannabinol or $\Delta^8$-tetrahydrocannabinol.

7. The method of claim 1 wherein the cannabinoid receptor agonist is a synthetic cannabinoid receptor agonist.

8. The method of claim 1 wherein the administration of the cannabinoid receptor agonist and the COX-2 inhibitor is systemic.

9. The method of claim 1 wherein the microvasculature is striated muscle microvasculature.

10. A method for countering the tendency of an administered cannabinoid receptor agonist to cause dilation of arterial musculature in a subject comprising co-administering to the subject a COX-2 inhibitor with the cannabinoid receptor agonist.

11. The method of claim 10 wherein the subject is a mammal.

12. The method of claim 11 wherein the mammal is a human.

13. A method for increasing blood pressure in a subject comprising co-administering an effective amount of a cannabinoid receptor agonist and a COX-2 inhibitor in an amount effective to increase blood pressure in the subject.

14. The method of claim 13 wherein the subject is a mammal.

15. The method of claim 14 wherein the mammal is a human.

16. The method of claim 13 wherein, at the time of the co-administration, the subject is suffering from an acute decrease in blood pressure.

17. A method for treating a subject suffering from or at risk of shock comprising co-administering to a vertebrate subject in need thereof a cannabinoid receptor agonist and a COX-2 inhibitor, wherein the amount of the COX-2 inhibitor that is administered is sufficient to provide a synergistic response pertaining to constriction of striated muscle arterial microvasculature when combined with the cannabinoid receptor agonist.

18. The method of claim 17 wherein the COX-2 inhibitor is also a COX-1 inhibitor.

19. The method of claim 17 wherein the COX-2 inhibitor is selected from the group consisting of rofecoxib, celecoxib, valdecoxib, paracoxib, etoricoxib, and NS-398.

20. The method of claim 17 wherein the cannabinoid receptor agonist is $\Delta^9$-tetrahydrocannabinol or $\Delta^8$-tetrahydrocannabinol.

21. The method of claim 17 wherein the cannabinoid receptor agonist is a synthetic cannabinoid receptor agonist.

22. The method of claim 17 wherein the administration of the cannabinoid receptor agonist and the COX-2 inhibitor is systemic.

23. The method of claim 17 wherein the subject is a mammal.

24. The method of claim 23 wherein the mammal is a human.

25. The method of claim 17 wherein the shock is hemorrhagic shock.

26. The method of claim 17 wherein the co-administration is to control hypotension associated with anesthetic agents.

* * * * *